United States Patent
Spagnolo et al.

(10) Patent No.: US 11,783,949 B2
(45) Date of Patent: Oct. 10, 2023

(54) METHODS AND SYSTEMS FOR SEVERITY CALCULATOR

(71) Applicant: ARIEL PRECISION MEDICINE, INC., Pittsburgh, PA (US)

(72) Inventors: Daniel M. Spagnolo, Pittsburgh, PA (US); David Whitcomb, Pittsburgh, PA (US)

(73) Assignee: Ariel Precision Medicine, Inc., Pittsburgh, PA (US)

( * ) Notice: Subject to any disclaimer, the term of this patent is extended or adjusted under 35 U.S.C. 154(b) by 451 days.

(21) Appl. No.: 16/700,014

(22) Filed: Dec. 2, 2019

(65) Prior Publication Data

US 2020/0176119 A1 Jun. 4, 2020

Related U.S. Application Data

(60) Provisional application No. 62/773,647, filed on Nov. 30, 2018.

(51) Int. Cl.
*G16H 50/30* (2018.01)
*A61B 5/00* (2006.01)

(52) U.S. Cl.
CPC .............. *G16H 50/30* (2018.01); *A61B 5/425* (2013.01); *A61B 5/4842* (2013.01); *A61B 5/74* (2013.01)

(58) Field of Classification Search
CPC .................. A61B 5/425; A61B 5/4842; A61B 5/72–5/7296; A61B 5/74–5/7495; G16H 50/30; G16H 50/00–50/80
See application file for complete search history.

(56) References Cited

U.S. PATENT DOCUMENTS

| | | | | |
|---|---|---|---|---|
| 7,395,216 B2* | 7/2008 | Rosenfeld | ............... | G16H 40/67 600/300 |
| 8,521,556 B2* | 8/2013 | Chbat | .................... | G16H 50/50 703/11 |
| 11,138,724 B2* | 10/2021 | Nakano | .................... | G06N 3/08 |
| 2006/0271407 A1* | 11/2006 | Rosenfeld | ............... | G16H 50/20 434/262 |
| 2007/0025977 A1 | 2/2007 | Mulberg | | |
| 2008/0305962 A1 | 12/2008 | Wirtz | | |
| 2009/0298061 A1 | 12/2009 | Wirtz | | |
| 2010/0081129 A1 | 4/2010 | Belouchi et al. | | |
| 2010/0169409 A1 | 7/2010 | Fallon et al. | | |
| 2010/0212675 A1 | 8/2010 | Walling et al. | | |
| 2010/0332249 A1* | 12/2010 | Chbat | .................... | G16H 50/50 703/2 |
| 2012/0157542 A1 | 6/2012 | Wirtz | | |

(Continued)

OTHER PUBLICATIONS

Iqbal, Umair, Hafsa Anwar, and Melissa Scribani. "Ringer's lactate versus normal saline in acute pancreatitis: A systematic review and meta-analysis." Journal of digestive diseases 19.6 (2018): 335-341. https://doi.org/10.1111/1751-2980.12606 (Year: 2018).*

(Continued)

*Primary Examiner* — Jonathan T Kuo
(74) *Attorney, Agent, or Firm* — DLA Piper LLP

(57) ABSTRACT

A severity calculator analyzes patient information including a patient avatar and a patient state and along with a patient trajectory calculator, computes a predicted outcome which is used to administer treatment. The severity calculator systems and computer program products are also disclosed.

16 Claims, 9 Drawing Sheets

(56) References Cited

U.S. PATENT DOCUMENTS

| | | |
|---|---|---|
| 2012/0184560 A1 | 7/2012 | Wong et al. |
| 2014/0378500 A1 | 12/2014 | Cohen et al. |
| 2018/0045730 A1 | 2/2018 | Cohen et al. |
| 2018/0350069 A1* | 12/2018 | Nakano ................ G06N 3/0454 |
| 2019/0057774 A1* | 2/2019 | Velez ..................... G16H 50/50 |
| 2021/0042700 A1* | 2/2021 | Tamano ................. G06F 17/15 |

OTHER PUBLICATIONS

Beyer, Georg. Mayerle, Julia. Simon, Peter. Lerch, Markus M. (2016). Fluid resuscitation in acute pancreatitis. Pancreapedia: Exocrine Pancreas Knowledge Base, DOI: 10.3998/panc.2016.1 (Year: 2016).*

Farkas, Hypercalcemia, The Internet Book of Critical Care, Apr. 6, 2023, https://emcrit.org/ibcc/hypercalcemia/#:~:text=Lactated%20Ringers%20is%20suboptimal%20because,use%20in%20patients%20with%20hypercalcemia. (Year: 2023).*

* cited by examiner

METHODS AND SYSTEMS FOR SEVERITY CALCULATOR

BACKGROUND

Tracking and assessing patients in various locations such as in the field, in living facilities, in medical offices, or in hospitals is a constant challenge. The challenge is heightened for conditions where early assessment of patient severity and a corresponding management of patient care is crucial in preventing rapid progression towards organ failure, irreversible tissue damage, other morbidities or mortality. However, clinicians have limited time and capacity to assess all potential information, and/or the amount or quality of the information may be limited by circumstances. In light of these problems, there is a continuing need for systems, methods, and computer program products that can quickly assess a patient's health state and assist clinicians in making decisions.

SUMMARY

This summary indicates the nature and substance of the invention and is submitted with the understanding that it will not be used to interpret or limit the scope or meaning of the claims.

In one embodiment, there is a severity calculator system, comprising a processor; and a non-transitory processor readable storage medium containing instructions executable by the processor to determine a patient state machine by collecting and transforming one or more of patient static measurements and patient dynamic measurements, determine a patient avatar, the patient avatar being substantially derived from at least one of a patient archetype model and a patient model, collect information from at least one user or device that performs at least one test associated with a disease state, determine the trajectory of a patient, wherein the trajectory of the patient is one or more of towards a healthy state, towards organ failure, and towards the disease state, and the trajectory of the patient is computed by a patient trajectory predictor, and determine and output at least one patient intervention that, when the patient intervention is performed, leads to homeostasis of a patient.

In another embodiment, the disease state is acute pancreatitis.

In another embodiment, the at least one patient intervention includes one or more of taking no action with respect to the patient, administering normal saline solution, administering dextrose solution, administering Ringer's lactate solution, administering albumin, administering plasma, or administering a solution of electrolytes.

In another embodiment, the instructions further cause the processor to choose an intervention and communicate with an infusion device.

In another embodiment, the instructions further cause the processor to compute a prediction error.

In another embodiment, the prediction error includes one or more of a mean square error, a sum of squared errors, a t-statistic, or a rule-based output.

In another embodiment, the prediction error is only based on the most recently predicted time point.

In another embodiment, the instructions further cause the processor to change the patient avatar based on the computed prediction error.

In another embodiment, the at least one test associated with a disease state is one or more of a measurement of blood pressure, respiratory rate, heart rate, serum electrolyte levels, blood urea nitrogen levels, blood creatinine levels, arterial blood gas levels, pH, pulse oximetry, imaging, blood cell count, urine output, fecal output, body temperature, blood sugar measurements, liver injury test, lipid profiles, serum protein levels, albumin levels, hormone levels, metabolome levels, and secretion levels.

In one embodiment, a severity calculator computer program product comprises a storage device having code stored therein, the code being executable by a processor and comprising code that determines a patient state machine by collecting and transforming one or more of patient static measurements and patient dynamic measurements, code that determines a patient avatar, the patient avatar being substantially derived from at least one of a patient archetype model and a patient model, code that collects information from at least one user or device that performs at least one test associated with a disease state, code that determines the trajectory of a patient, wherein the trajectory of the patient is one or more of towards a healthy state, towards organ failure, towards the disease state, and the trajectory of the patient is computed by a patient trajectory predictor, and code that determines and outputs at least one patient intervention that, when the patient intervention is performed, leads to homeostasis of a patient.

In another embodiment, the disease state is acute pancreatitis.

In another embodiment, the at least one patient intervention includes one or more of taking no action with respect to the patient, administering normal saline solution, administering dextrose solution, administering Ringer's lactate solution, administering albumin, administering plasma, or administering a solution of electrolytes.

In another embodiment, the severity calculator computer program product further comprises code that chooses an intervention and code that communicates with an infusion device.

In another embodiment, the severity calculator computer program product further comprises code that computes prediction error.

In another embodiment, the prediction error includes one or more of a mean square error, a sum of squared errors, a t-statistic, or a rule-based output.

In another embodiment, the prediction error is only based on the most recently predicted time point.

In another embodiment, the instructions further cause the processor to change the patient avatar based on the computed prediction error.

In another embodiment, the at least one test associated with a disease state is one or more of a measurement of blood pressure, respiratory rate, heart rate, serum electrolyte levels, blood urea nitrogen levels, blood creatinine levels, arterial blood gas levels, pH, pulse oximetry, imaging, blood cell count, urine output, fecal output, body temperature, blood sugar measurements, liver injury test, lipid profiles, serum protein levels, albumin levels, hormone levels, metabolome levels, and secretion levels.

In one embodiment, a method of calculating severity comprises: determining a patient state machine by collecting and transforming one or more of patient static measurements and patient dynamic measurements, determining a patient avatar, the patient avatar being substantially derived from at least one of a patient archetype model and a patient model, collecting information from at least one user or device that performs at least one test associated with a disease state, determining the trajectory of a patient, wherein: the trajectory of the patient is one or more of towards a healthy state, towards organ failure, towards the disease state, and the trajectory of the patient is computed by a patient trajectory predictor, and determining and outputting at least one patient intervention that, when the patient intervention is performed, leads to homeostasis of a patient.

In another embodiment, the disease state is acute pancreatitis.

BRIEF DESCRIPTION OF THE DRAWINGS

Aspects, features, benefits and advantages of the embodiments described herein will be apparent with regard to the following description, appended claims, and accompanying drawings where:

DETAILED DESCRIPTION

Figure 1:
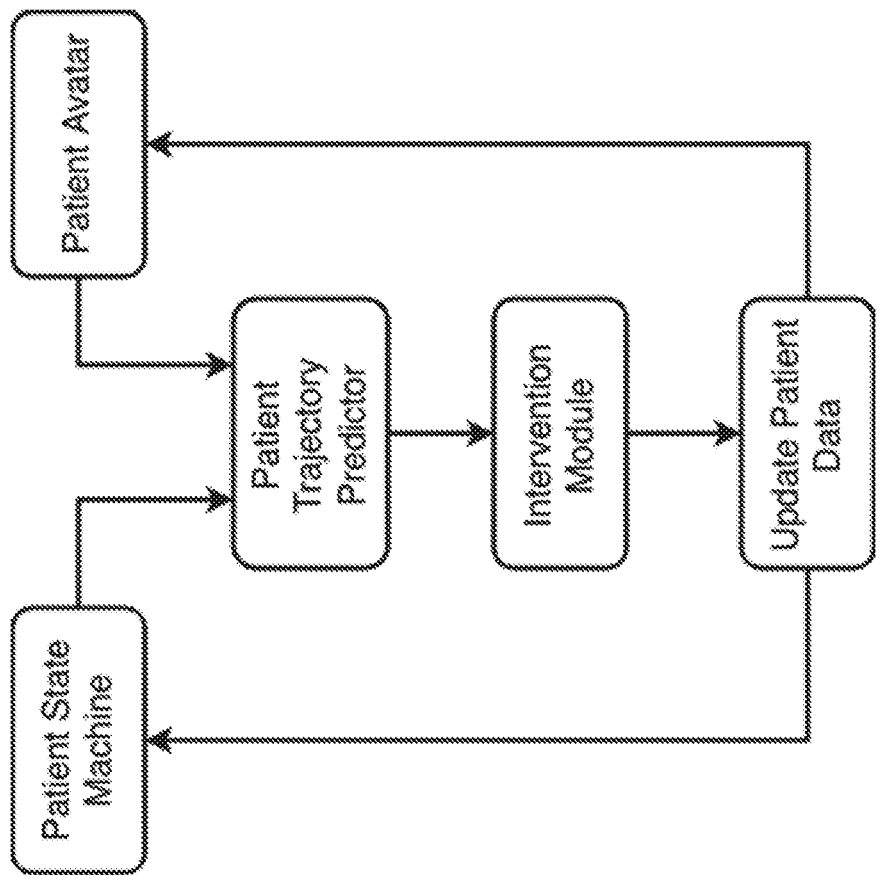
FIG. 1 is a block diagram of an embodiment of the severity calculator.

Referring now to FIG. 1, an embodiment of a severity calculator 1 is depicted. In the embodiment, the severity calculator 1 includes a patient avatar, a patient state machine, a patient trajectory calculator, an intervention module, and a dynamic patient data module that interact with each other.

In some embodiments, a patient avatar is a systems model of the patient that is based on a standardized patient model and is improved as more patient information becomes available. In some embodiments, the patient model is a patient archetype that simplifies the grouping, categorization, processing, and other actions that are performed on the patient avatar. The patient avatar models one or more of a patient's internal physiological functions and systems under various conditions allowing for more accurate management. In one embodiment, the patient avatar can approximate a complete representation of the patient. In another embodiment, the patient avatar can approximate systems related to specific conditions. In still further embodiments, the patient avatar can approximate groups of related body systems which are related to specific conditions. In other embodiments, the patient avatar may be representative of unrelated body systems which have little or no effect on each other.

The patient state machine encompasses patient characteristics. These patient characteristics may include static measurements (e.g. demographic information) and dynamic measurements captured via clinician observations, laboratory tests, and medical devices. In an embodiment, the patient characteristics may include some or all measurements recorded for the patient and may be taken from one or more sources. In an embodiment, each set of measurements represents a snapshot of the patient, or a portion of the patient, at a given time. As described in more detail below, this progressive documentation allows for more accurate assessments and predictions as well as more accurate patient modeling.

The patient trajectory calculator uses the patient avatar and the patient state machine to determine the most likely course of progression regarding the patient's condition. Using patient specific models of underlying physiological functions, i.e., the patient avatar, as well as the patient's current and past states, the patient trajectory calculator assesses the patient's severity and predicts the natural course of the condition and how various interventions will affect one or more patient physiological functions. The interventions may be interventions that are specific to a particular condition or set of conditions. Alternately, the interventions may be common to most conditions, such as patient supportive care.

After assessing the patient's severity and predicting a patient's reaction to zero, one or more interventions, the intervention module suggests suitable courses of action for managing the patient's condition. In an embodiment, an intervention can be selected based on how the patient, overall, will react compared to the patient's reactions to other interventions. In an embodiment, the intervention module can provide a ranked list of interventions along with descriptions of each outcome. With the ranked list and outcomes, a clinician may then choose a new patient management approach incorporating insights, recommendations, or other actions. While it is appreciated that a clinician in some embodiments will utilize the ranked list and outcomes to select a patient approach, it is appreciated that the ranked list and outcomes may be disregarded or followed unquestioningly depending on circumstances.

The patient state may be captured at any time. In some embodiments, the patient state is captured before an intervention is selected. In further embodiments, the patient state is captured during the intervention. In further embodiments, the patient state may be captured after the intervention is selected. Combinations of these may also be selected for capture. In each instance, the information captured at these points is used to update the patient's state machine and also to improve the patient's avatar.

In an embodiment, a captured patient state can be compared to a previous patient's state as well as a predicted patient state. In an embodiment, a patient's state and a patient's predicted state each comprise multiple state measurements. In an embodiment, multiple state measurements can be used to analyze patient system trajectories to assemble the patient's state machine and improve the patient's avatar.

As discussed above, and described in more detail below, the severity calculator can be used in a number of different situations. For example, in one embodiment, the severity calculator can be used on a patient presenting with acute pancreatitis symptoms (e.g. elevated amylase and lipase in the blood, sudden onset of abdominal pain, nausea or vomiting). In such an embodiment, the severity calculator would monitor treatment, especially within the first 48 hours where early intervention is important, determine an appropriate fluid resuscitation strategy, and relay corresponding information to an infusion device. In another embodiment, the severity calculator is used on a patient with severe burns to mitigate presentation of shock and assist in preventing further organ damage. In another embodiment, the severity calculator is used on a patient with trauma or hemorrhage to minimize the effects of altered physiology and damage signals. In another embodiment, the severity calculator monitors a patient with type 1 or type 2 diabetes, distributing insulin as needed. In still further embodiments, the patient archetype may be used to predict a greater or less severe response to an injury or insult, a higher or lower resistance to a stress state, a higher or lower likelihood of dysfunction or failure of one or more organs to an injury, burn, sepsis, hemorrhage or acute pancreatitis that may be used to determine acceptable levels of risk for various situations, such as high risk jobs in sports, law enforcement, military combat or combinations of the above. It is appreciated that these embodiments are exemplary, and that the severity calculator may be deployed for a variety of different settings and purposes. In some embodiments, the deployment of the severity calculator is characterized by its location, such as at home, at a primary care office, in a hospital, at an urgent care facility, or a battlefield where interventions may or may not be determined and applied via clinicians and/or hospital devices. In some embodiments, the severity calculator is a discrete device or system that gathers data to model and manage patient care, for example at an urgent care facility, other local office or a battlefield. In some embodiments, the severity calculator is integrated to manage a patient's care even before the onset of any outward symptoms. For example, the severity calculator may be part of a patient's primary care facility or used in conjunction with the patient's primary care services.

The Patient Avatar

Figure 2:
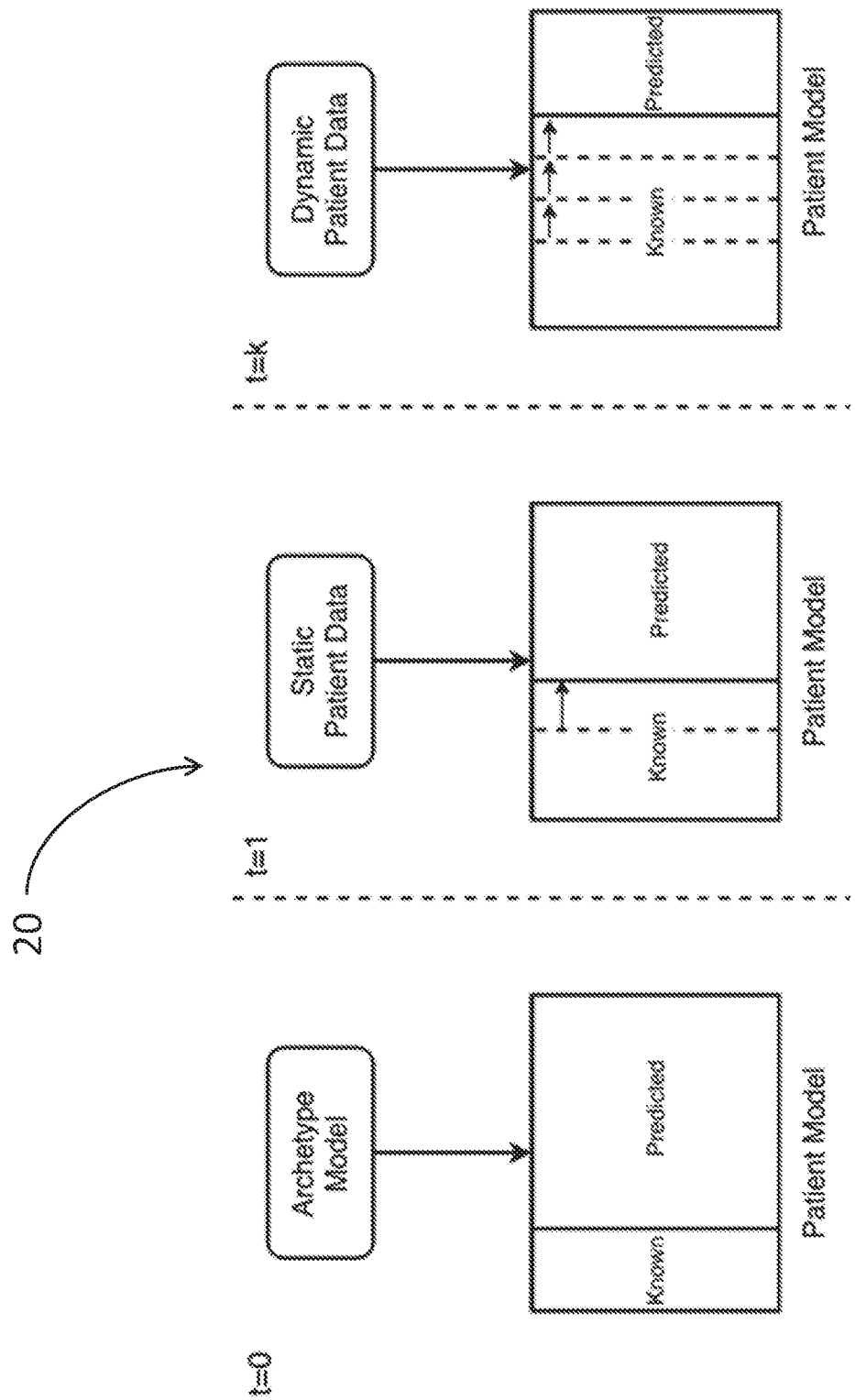
FIG. 2 is an illustration of an embodiment of the patient avatar.

Referring now to FIG. 2, a patient avatar 20 is depicted. As described above, the patient avatar is a component of the severity calculator. Patient archetypes, which will be described in more detail below, define a generic representation of a typical person's physiology. During operation and computation, the patient avatar 20 develops into a continuously improving model of a specific patient's physiological systems. At any given point in time, some portion of the model is predicted based on patient specific data while the rest of the patient model is a prediction based on the archetype. This is best shown by the progression in FIG. 2, where the area of each box represents the relative richness of the data set and/or the volume of data available for computation.

The archetype model is a model system or family of systems derived from real or imaginary components, that may include, but are not limited to measures in one or more subjects from one or more populations or species and principles of epidemiology, biology, systems, physics, mathematics, modeling, thresholds, trajectories and other components that may be relevant to the severity calculator. In one embodiment, the patient archetype may include fluid compartments that represent a vascular compartment, cellular compartment, interstitial compartment, lymphatic compartment, and/or specific tissue compartments such as the lungs, gastrointestinal, cardiovascular system, renal system and additional spaces. In another embodiment, the compartments may have specific volumes, dimensions, pressures, and contents; and may be organized with defined interfaces, linings, permeabilities, functions, secretions, absorptions, fluxes, electric potential differences, or other components. In another embodiment, the patient archetype may contain virtual compartments that are lined by structures, substances, barriers, and/or specialized cells that have defined functions, activities, actions, reactions, responses, and dynamics under one or more conditions. In another embodiment, the patient archetype may be defined by, but not limited to, specific genetic, genomic, proteomic, metabolomic, biome, medications, xenobiologics, environmental, traumatic, historical, or other factors that may be derived from the study of one or more subjects. In another embodiment, the patient archetype may include, but is not limited to, equations, patterns, probability distributions, examples, and/or associations to represent dynamic effects, outcomes, surrogate outcomes, and other tools used in the severity calculator.

In some embodiments, the severity calculator includes a process in which one or more archetype models are selected as the patient archetype(s) for constructing the patient avatar. In some embodiments, the patient archetype is a "standard person" or "70 kg man," each of which may be used to approximate a healthy young adult. Of course, multiple patient archetypes can be used to represent patients. In another embodiment, the patient archetype could represent a typical patient with mild acute pancreatitis. In another embodiment, the patient archetype could represent a patient with more severe acute pancreatitis, representing a patient that would require transfer from a general hospital. It is appreciated that variations on the above archetypes are permissible, such as alterations depending on a specific disease type. Still further, the archetype may be modified or based on various physiological factors including sex, ethnicity, height, weight, age, blood pressure, and combinations of the above. Still further, the archetype may be modified or based on genetic or genomic data or surrogate markers associated with normal or altered function of the systems that it codes for either directly or indirectly, or derivatives of gene function or lack of function that are relevant to an archetype or avatar.

Following the definition and selection of the patient avatar, a patient model is formed using static patient data. Such static patient data does not change over time. In one embodiment, the static patient data includes sex, ethnicity, height, weight, family history of disease, genetic information, genetic predispositions, past medical history, past surgical history, and combinations of the above. In some embodiments, the data does not change over the course of multiple seconds, minutes, or days. The incorporation of additional static data increases what is known in the patient model, and shrinks the relative proportion of the predicted data from the patient archetype.

In addition to the above-described static patient data, dynamic patient data is continuously used to refine the patient model. This data may take the form of one or more patient vitals and lab tests recorded by a clinician or device. Dynamic data may include blood pressure measurements, respiratory rate, heart rate, serum electrolyte levels, blood urea nitrogen and creatinine measures, arterial blood gas measurements, pH measures, pulse oximetry, imaging tests, blood cell count, urine output, fecal output, body temperature, blood sugar measurements, liver injury test, lipid profiles, serum proteins including albumin, hormone measurements, metabolome measures, secretion measurements, imaging studies, and combinations of the above. It is appreciated that these are merely examples and that dynamic patient data may take a variety of forms.

Patient Model

Figure 3:
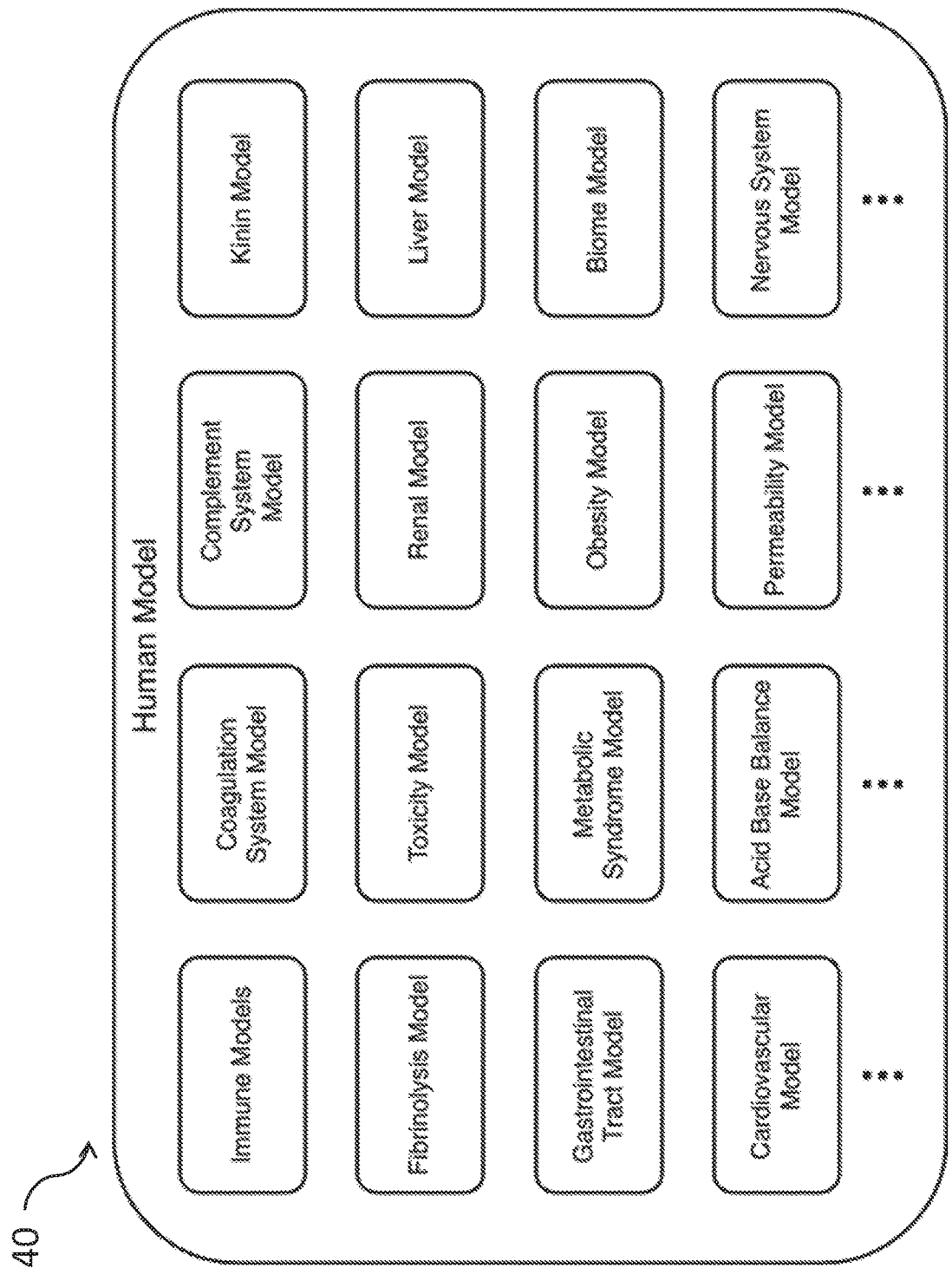
FIG. 3 is an illustration of an embodiment of the patient model.

Referring now to FIG. 3, the patient model 40 models a patient's internal physiological functions. The patient model includes many submodels which represent contained systems within the patient, that may be initially based on one or more patient archetypes. Together with static data and dynamic data from the patient avatar, the patient model can be used to inform how each of the submodels functions and interacts with other submodels. In an embodiment, each of these submodels are mathematical models, formalized by a set of variables and a set of equations that describe relationships between the variables. In an embodiment, some models may be rule-based, or mixed models. In an embodiment, the patient model can be used to analyze where on the spectrum of health a given patient resides. In an embodiment, this may inform how severe a patient's condition is. In an embodiment, the patient model includes as many of the submodels as are available. In an embodiment, the patient model only includes specific submodels, for example those related to lung function and blood oxygenation, cardiovascular function, vascular function and permeability, fluid status and resuscitation, pancreatitis, diabetes, insulin, or the like, or combinations of the above.

In some embodiments, the submodels have direct and indirect consequences on other components in the patient model. For example, some submodels within the patient model represent the behavior or individual organs or organ systems. This includes but is not limited to a renal model, a liver model, a cardiovascular model, a gastrointestinal model, a nervous system model, etc. Other major submodels include the immune, complement, kinin, and fibrinolysis models, which interact within the context of inflammation, coagulation, and immunity. One example of a direct effect of one submodel upon another would be an abnormality in an endocrine submodel, e.g. hypothyroidism having a direct effect on a patient's obesity model, contributing to weight gain. An example of indirect effect could be a change in the cardiovascular model, e.g. increased blood flow, effecting the gastrointestinal model by increasing nutrient absorption, which then effects a third submodel, for example by improving neurological function from enhanced nutrition. In another embodiment, submodel interactions in pancreatitis may be a perturbation in a feeding model or a fluid compartment model leading to hypovolemia, e.g via third space extravasation, reduced oral intake, or vomiting, leading to an effect in the cardiovascular model of reduced oncotic pressure, resulting in oxygen deprivation in the pancreatitis, and increasing risk for pancreatic necrosis.

Patient Trajectory Predictor

Figure 4:
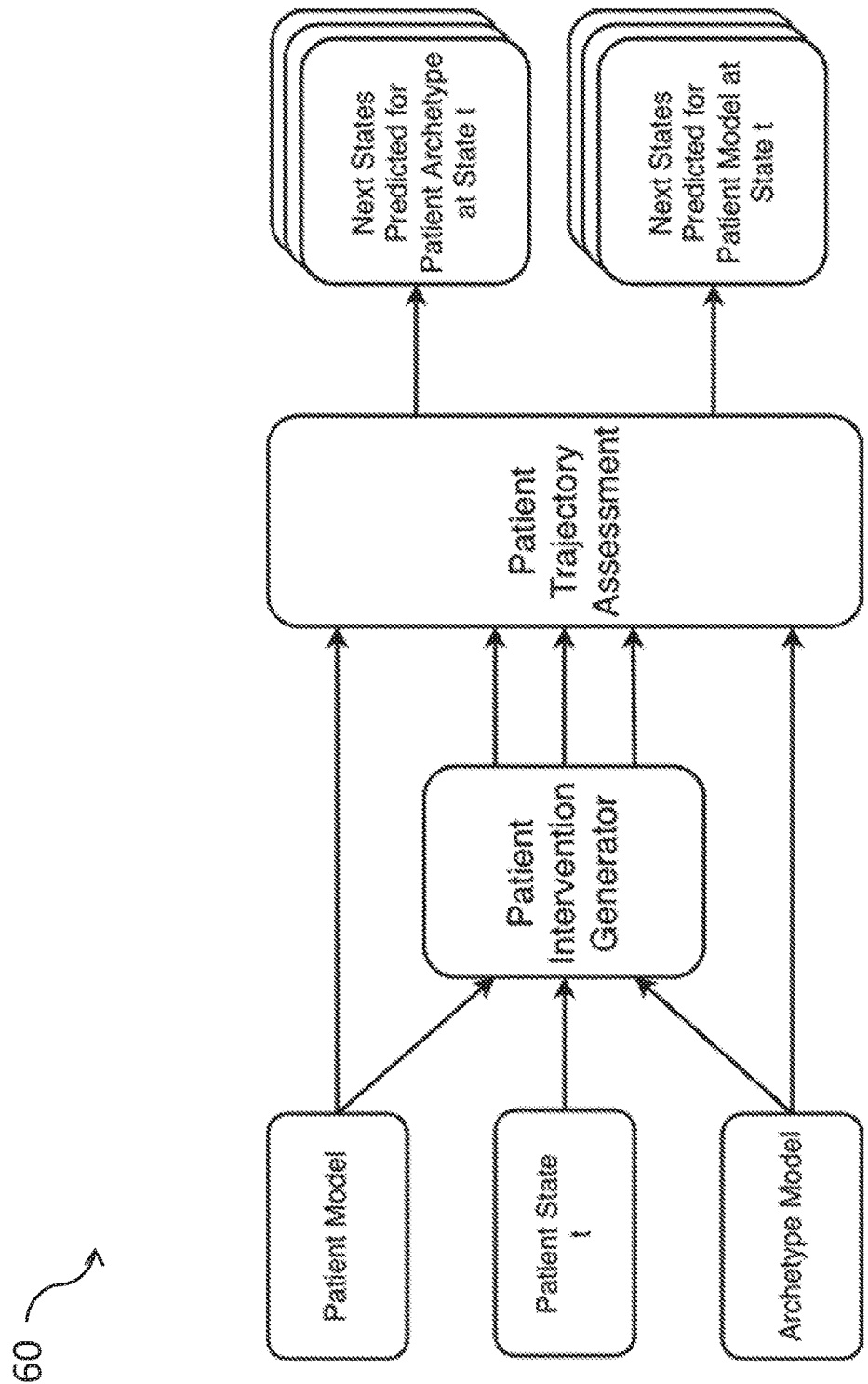
FIG. 4 is an illustration of an embodiment of the patient trajectory predictor.

Referring now to FIG. 4, the patient trajectory predictor 60 allows a clinician to understand the current trends that are associated with a patient. The trends include towards a healthy state, towards organ failure, towards a particular disease state, and combinations of the above. The patient trajectory predictor offers a holistic analysis of patient outcomes related to multiple interventions, organizes important considerations toward care, and considers how the patient has been trending from symptom presentation to hospital admission to current patient status.

As input, the patient trajectory predictor considers all components of the patient avatar (including patient archetype and patient model), and the patient's current state as stored in the patient state machine. The patient trajectory predictor provides an informed decision, based on the patient model and state, of the most likely next state of the patient at one or more time steps in the future. The patient trajectory predictor predicts what the next state would be for the archetype, as well as the patient with and without myriad interventions as produced by the patient intervention generator. Many different interventions are considered and their effect on future patient state are predicted in all cases. For example, a patient presenting with sepsis shock may have different intervention options including fluid resuscitation and maintenance with several different potential fluid types (e.g. normal saline, dextrose solution, lactated ringers solution, or solutions of electrolytes such as the commercially available PLASMA-LYTE A from Baxter International, Inc). The interventions might also include changing to a faster or slower flow rate of fluids, or the amount of total fluids within a given duration. The patient trajectory predictor for a patient with sepsis shock already receiving fluids might predict how the patient would fare under the same fluid regimen, under a more aggressive fluid regimen, and under a less aggressive fluid regimen. It is appreciated that the disclosure is not limited and that other interventions are possible, as are different predictions of the patient's future state under a variety of conditions. Interventions may include intravenous, arterial, epidural infusions, temperature by heating or cooling the patient, and combinations of the above.

Patient Trajectory Assessment

Figure 5:
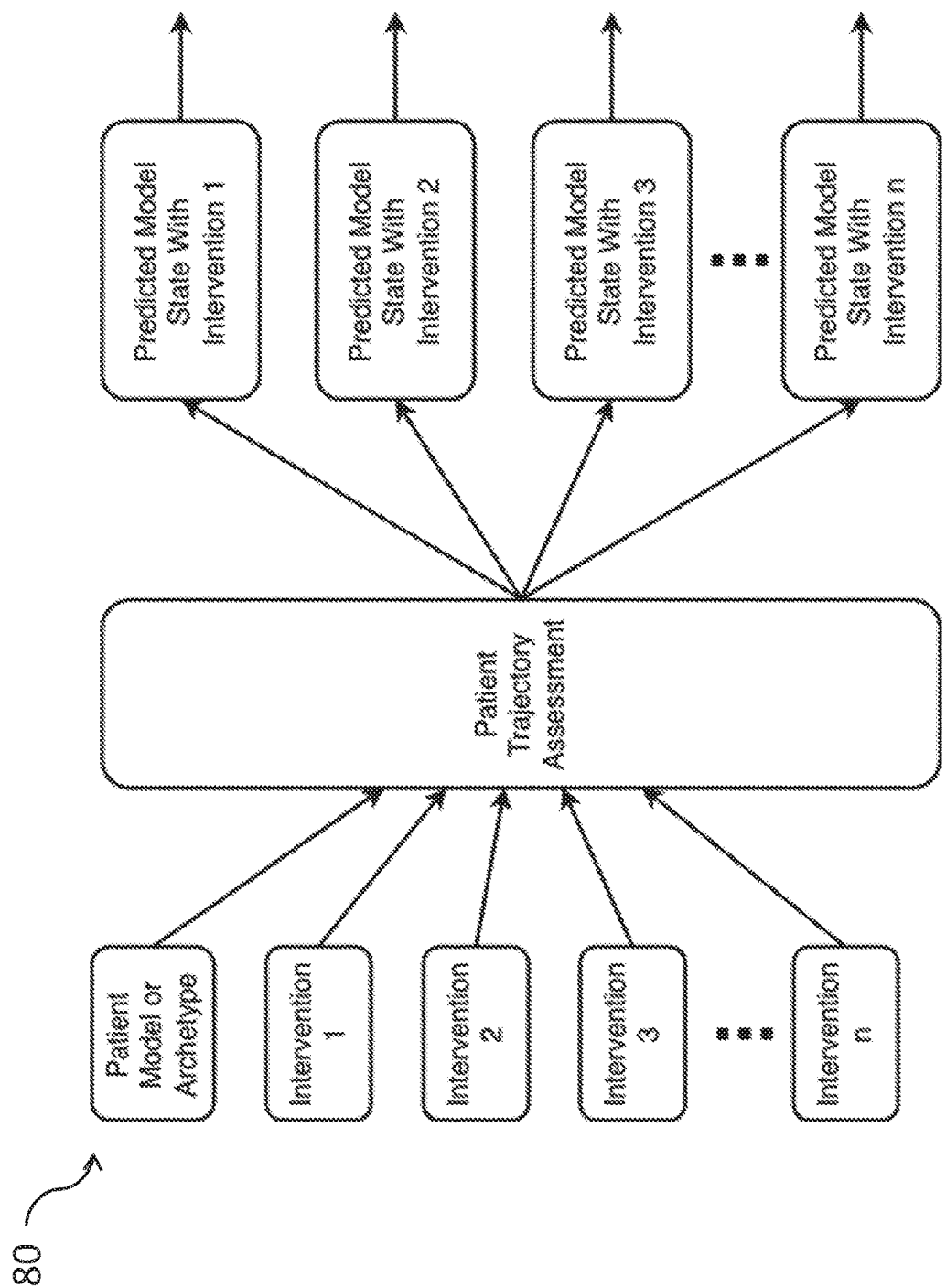
FIG. 5 is an illustration of an embodiment of the patient trajectory predictor.

Referring now to FIG. 5, patient trajectory assessment 80 describes various steps and actions that may be taken for a given patient model or patient archetype. The patient trajectory assessment predicts the next state of the model given an intervention as produced by the patient intervention generator. In one embodiment, where a patient is exhibiting blood loss, fluid replacement strategies may be suggested to replace the lost volume. One suggested intervention may be to use a standard crystalline volume expander such as normal saline. Another suggested intervention might be to use Ringer's lactate as the crystalloid fluid, for example if the patient was also exhibiting metabolic acidosis. A third intervention might suggest a dextrose and water formulation, with the goal of replacing a water deficit. Yet another intervention might suggest a colloid volume expander such as albumin, plasma or a solution with components of a molecular size and composition to compensate for changes in volumes, permeabilities or fluxes between compartments. Other interventions may increase or decrease the flow or daily limit of these different volume expanders. While the example of a patient exhibiting blood loss is given, it is appreciated that the disclosure is not so limited and may encompass other potential conditions such as those described elsewhere in the specification. The patient trajectory assessment predicts the next model state under each of these interventions. In an embodiment, this model may be the patient model. In an embodiment, this model may be the patient archetype.

Intervention Module

Figure 6:
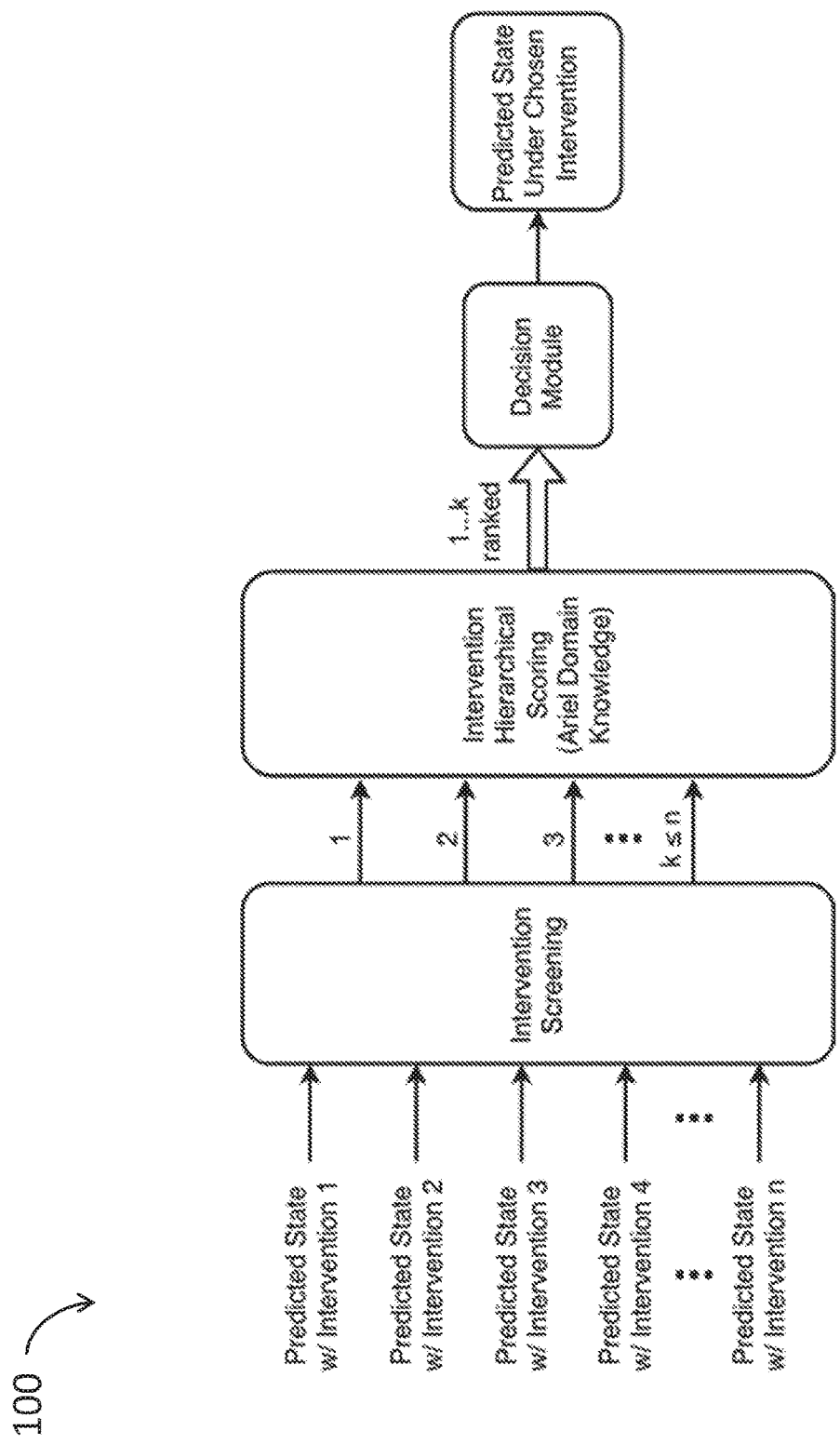
FIG. 6 is an illustration of an embodiment of the intervention module.
Figure 7:
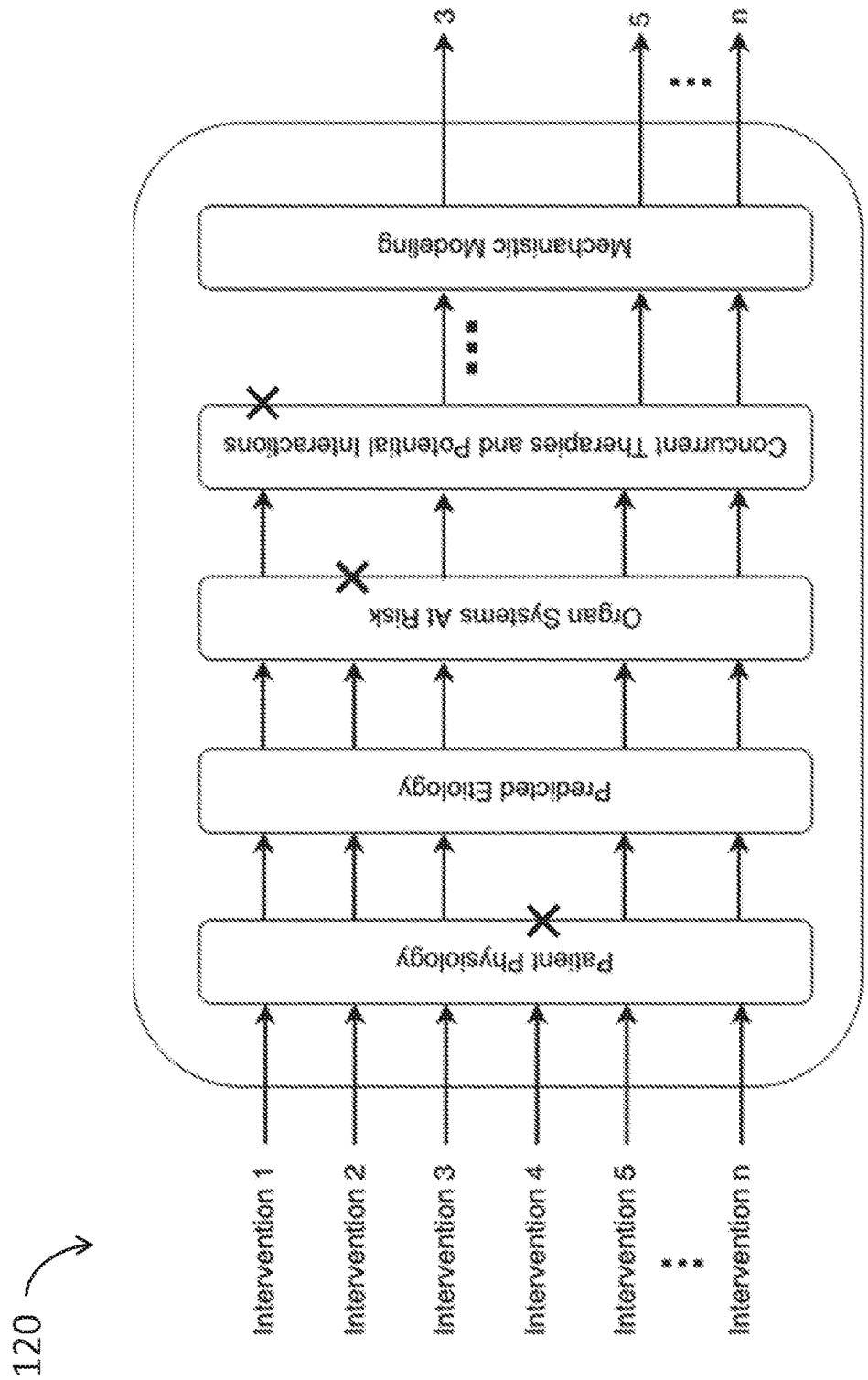
FIG. 7 is an illustration of an embodiment of the intervention screening.

Referring now to FIG. 6, the intervention module 100 suggests one or several interventions most likely to lead to patient homeostasis while the patient trajectory predictor checks the patient states. First, the intervention module includes an intervention screening step, as shown in FIG. 7. In FIGS. 6-7, each intervention may be recommended based on a particular malady in the patient. For example, one intervention might be suggested to counteract abnormal hematocrit levels, while another intervention might be suggested to address a high blood-urea-nitrogen-to-creatinine ratio. In some embodiments, the intervention screening step disqualifies certain interventions based on the patient's avatar or other information such as weight (e.g obesity, underweight), past disease history (e.g. history of heart disease), medical history (e.g. allergy to a particular intervention), predicted etiology (e.g. disqualifying lactated ringers solution bolus in hypercalcemic patients), or other factors. It is appreciated that the disclosure is not limited and that interventions would be considered in the context of a variety of patient conditions, and that interventions can be screened using a variety of heuristics and techniques.

After the screening, the remaining interventions are then scored and ordered into a hierarchy of patient interventions from promising to less favorable. In an embodiment, this hierarchical scoring can be based on a variety of coded rules and decision trees. Finally, a decision must be made for the best intervention. In one embodiment, the decision module is a manual system in which the clinician reviews and considers all interventions and predicted patient states, chooses the best intervention using this information and informed by their own experiences, and administers the intervention. In another embodiment, the decision module chooses the highest ranked intervention or uses a set of coded rules to choose an intervention and administers the intervention through a connected hospital device (e.g. infusion device). It is noted that any combination of the above may be employed.

Update Patient Data Module

Figure 8:
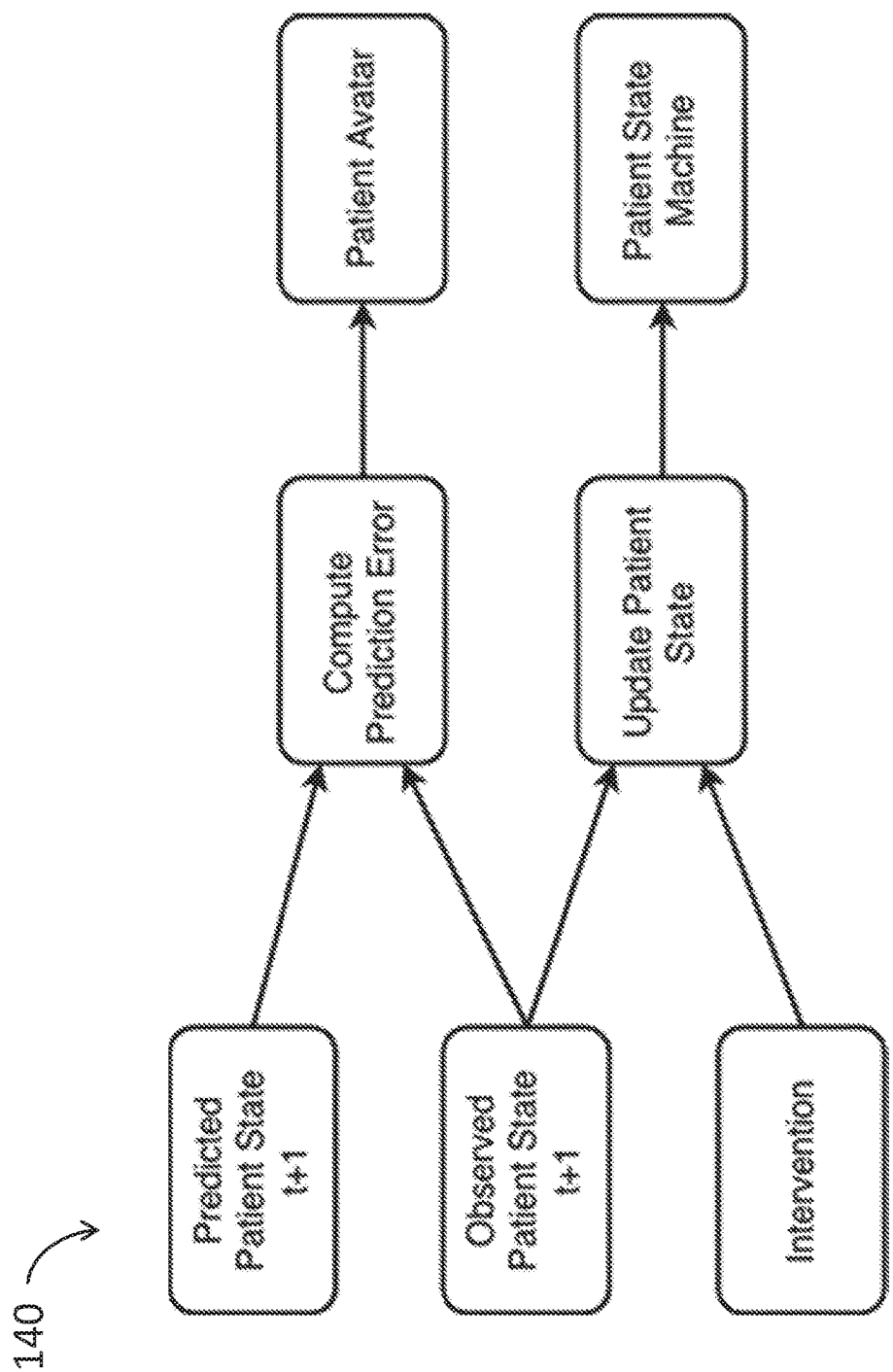
FIG. 8 is a block diagram of the update severity calculator.

After applying a particular intervention, including deciding not to perform an intervention or electing to continue with a current treatment plan, the severity calculator may be updated in preparation of predicting the following time point and future potential interventions (see FIG. 8). The actual observed patient state and intervention followed is recorded and saved in the patient state machine to undergo another round of severity calculator processing. Additionally, the observed patient state and predicted patient state are used to refine the patient avatar by assessing where the prediction was accurate and where it was potentially inaccurate.

In one embodiment, a module may compute prediction error. Such modules for computing prediction error can improve the patient avatar. The inputs to this module are the predicted and observed patient state. In some embodiments, the prediction error can be represented by any number of errors or residuals, e.g. mean square error, sum of squared errors, t-statistics, and/or rule-based outputs. In an embodiment, the prediction error is based only on the most recently predicted time point, though multiple or the entirety of states stored in the patient state machine can also be considered. In an embodiment, the predicted patient state after a dextrose fluid intervention could include reduced heart rate and increased systolic blood pressure as signs of improving previous presentation of hypovolemia. However, an unknown or undisclosed health condition, such as mild congestive heart disease, could result in unpredicted adverse effects from the chosen intervention. Overhydration in this case could lead to congestive heart failure, pulmonary edema, and/or related cardiovascular issues. The patient avatar could then be updated to reflect a more accurate representation of the patient for future operation of the severity calculator. In another embodiment, an intervention may be suggest to retain the current fluid management regime and the predicted next state of the patient may include improved vitals readings.

Patient Archetypes

Figure 9:
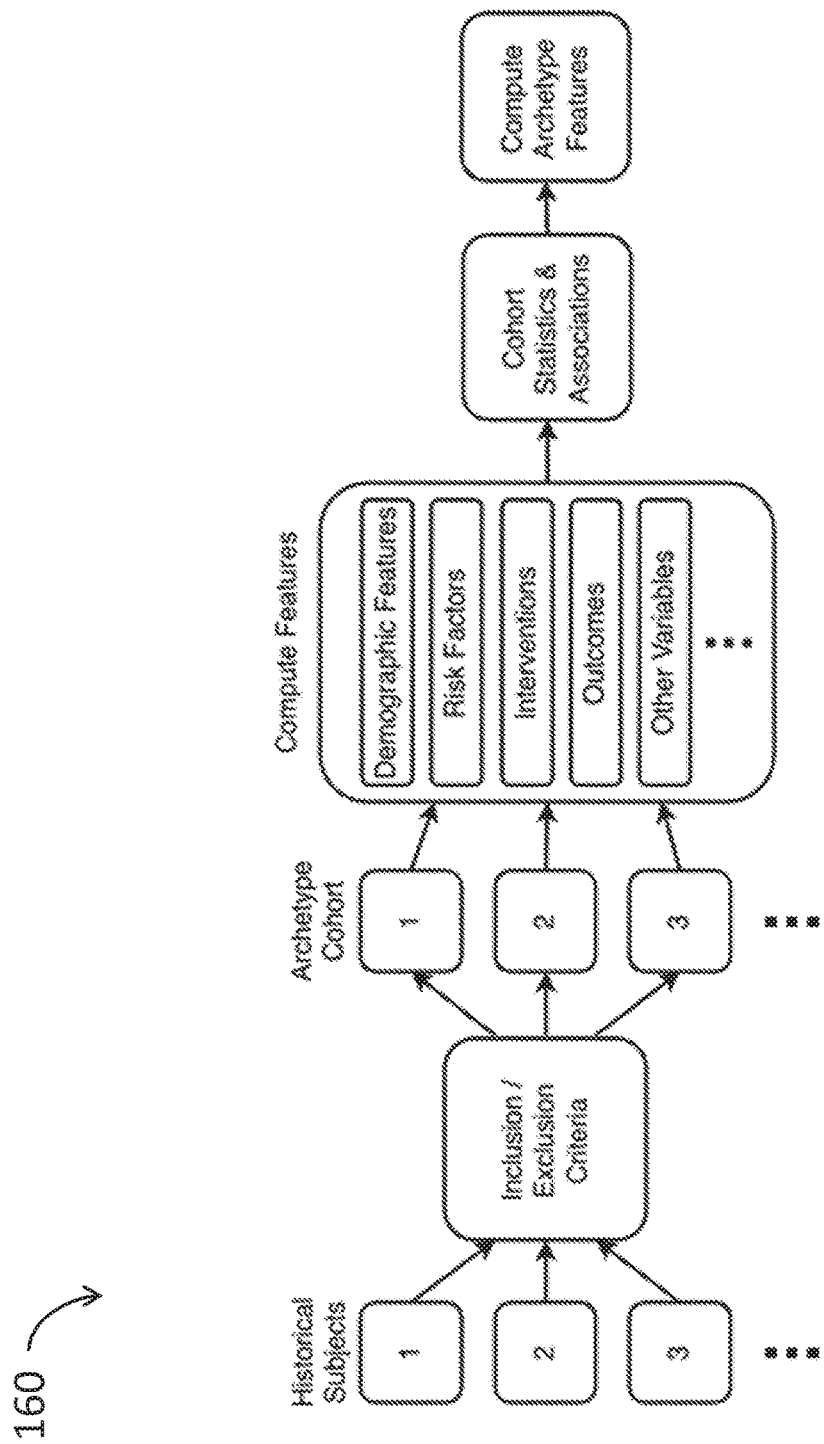
FIG. 9 is an illustration of the process of archetype model creation.

The severity calculator utilizes multiple patient archetype models. Referring now to FIG. 9, multiple archetype models are disclosed. As described above, a patient archetype model is preferably selected to match one or more features of the patient, and the patient avatar may be informed by one or more patient archetypes. The archetypes may represent normal conditions or dynamic conditions. In one embodiment, the patient archetype models selected to inform a patient avatar may represent subjects from a reference source of a similar age, sex, ancestry, and body mass who suffer a similar malady, such as acute pancreatitis. Since patients differ from one another on multiple levels, an archetype provides information on a limited number of features, based on previous measures, including, but not limited to, risks, biomarkers, states, conditions, outcomes, and surrogate outcomes. As more patients are observed and more information is collected under a given condition, more specific and fine-tuned patient archetypes may be developed.

In an embodiment, a more fine-tuned patient archetype results in a more accurate patient avatar at time t=0, since the avatar is initialized by the patient archetype, resulting in known and predicted attributes of the avatar. In another embodiment, a more fine-tuned patient archetype can be used as a baseline comparison against the patient avatar in a very specialized disease or condition.

FIG. 9 highlights how new patient archetypes can be constructed. Historical subjects are collected, in one embodiment through a hospital database, in another embodiment through literature search, and in yet another embodiment through private curation. A person of ordinary skill in the art would understand that these are just examples, and historical data can be collected from many additional sources and data from multiple difference sources can be used concurrently. Subjects are added to, or not added to, the sequential archetype models using inclusion/exclusion criteria resulting in a curated archetype cohort. A feature vector is computed for each subject in the cohort. In an embodiment, this feature vector might include demographics about the given patient, the intervention the patient received, and how the patient responded to the intervention (e.g. if the patient experienced complications, organ dysfunction, or mortality). Cohort statistics and associations are computed on the collection of feature vectors. In an embodiment, the intersection of features across cohort subjects is recorded. In another embodiment, the average of features across cohort subjects is recorded. The patient archetype features are a result of the cohort statistics and associations.

In an embodiment, the consequence of an injury, stress, insult, or other perturbation upon the archetype model is used to simulate the responses of the archetype patient. These results under a variety of conditions can be compared to the outcome of the human subjects of the archetype cohort at one or more time points for one or more conditions. In an embodiment, comparisons between the patient archetype and archetype cohort subjects may be used to alter or refine one or more variables of the archetype patient and thus improve the performance of the simulation. In another embodiment, the differences in responses between the archetype model and the patient avatar may be used to modify or replace a portion or more of the archetype model to better inform the patient avatar such as the one shown in FIG. 8.

Severity Calculator—Specific Embodiments

The following embodiments are not intended to be limiting, and each of the following embodiments may be used alone or in combination. An embodiment of the severity calculator is for the management of a patient with acute pancreatitis, although a person of ordinary skill in the art would recognize that the severity calculator is designed to be used in many other types of injury, traumas, burns, sepsis, inflammatory reactions or diseases. In the case of acute pancreatitis an early diagnosis and appropriate treatment is critical to improve outcomes compared to late or insufficient treatment. In this case, patient archetypes may be derived from the medial literature describing a series of patients with acute pancreatitis from defined populations, with defined inclusion/exclusion criteria, risk factors, biomarkers and/or outcomes at one or more time points. Examples of such studies may be found in severity scoring system validations and may be derived from groups of patients, each using different populations and different sets of features, with different implications, that can be used alone or in combination. Examples of validated scoring systems for acute pancreatitis include: APACHE-II, BISAP (Bedside Index of Severity in Acute Pancreatitis), Glasgow-Imrie, HAPS (Harmless Acute Pancreatitis Score), JSS (Japanese Severity Score), Panc 3, POP (Pancreatitis Outcome Predictor), Ranson and SIRS (Systemic Inflammatory Response Syndrome). In addition, the modified Marshall Score is used to evaluate organ dysfunction, the Pancreatitis Activity Scoring System (PASS) score is used to calculate disease activity prior to hospital discharge, and the Revised Atlanta Score (RAS) and the Determinant-Based Classification system are post-hoc severity classification tools.

In an embodiment of the severity calculator, the measures from a patient at any time point from the approximate onset of acute pancreatitis may be used to select a patient archetype derived from one or more populations used to generate or validate a scoring system. The available data may be used to model the status, severity, and/or predicted outcome of the patient as simulated by the patent avatar (see FIG. 2). In an embodiment where there is not sufficient data to calculate a severity or predicted outcome using one or more scoring systems, a process of using surrogate measures is invoked. One example of computing surrogate measures is using a pulse-oximeter to indirectly capture the patient's oxygen saturation which can be used to impute arterial partial pressure of oxygen (PaO2), if the fraction of inspired oxygen is known. Another example is to impute the components of total plasma protein using surrogates of total protein and albumin levels, preferably at multiple time points, and preferably including measure taken before the onset of acute pancreatitis. In an embodiment, the severity calculator provides information to one or more independent agents, such as a physician, to assess the suggestions from the patient trajectory predictor and intervention module. In an embodiment, the severity calculator may execute the suggested interventions, if desired, and order additional measures and/or lab tests at one or more time points. One example of this embodiment is to order additional diagnostic and monitoring tests if acute pancreatitis is suspected from an elevated amylase or lipase level in the blood. These tests may include measures of serum electrolytes, a lipid panel, a complete blood count, a protein panel with total protein and albumin, serum calcium levels, serum lipids, arterial or venous pH, measures of pulmonary function, cardiovascular function, kidney function, and other measures that are needed, or may be needed, to inform the severity calculators, to measure disease progression, or to measure response to therapies.

Another embodiment of the severity calculator uses the patient avatar to calculate predicted fluid compartment sizes, contents, features, and permeability between compartments. Information including, but not limited to, the history and ongoing observations of fluid intake, vomiting, diarrhea, sweating and urine output, measures of cardiovascular function such as heart rate, blood pressure, pulse pressure, and/or orthostatic blood pressures, respiratory rate, electrolyte concentrations including sodium, chloride, potassium, bicarbonate, CO2, blood urea nitrogen (BUN), creatinine or their surrogates, complete blood count including hemoglobin and hematocrit, total protein, albumin, triglycerides, blood pH, urine electrolytes and physical measures of dehydration such as dry skin, mucus membranes, lung sounds, heart sounds and gastrointestinal sounds may be used. In an embodiment, the severity calculator evaluates one or more of the measures compared to previous measures in the subject including the patient's baseline measurements (i.e. before the onset of acute pancreatitis), or estimates one or more of the measures from one or more patient archetypes. For example, the severity calculator could determine if there is a change in the permeability of various vascular beds causing shifts in fluids. In one case, an increase in blood hematocrit (the percent of blood made up of red blood cells) may indicate a decrease in the plasma compartment size associated with change in permeability (known as vascular leak). The leak may be reversible if linked to a reaction of the endothelial cells, or irreversible if linked to damage to the endothelial cells. In an embodiment, the area of altered vascular compartment permeability can be calculated from the rate of change in compartment volumes using the severity calculator. In another embodiment, the relative diameter of the area of permeability can be estimated from a surrogate measure of the relative change in larger molecules, such as immunoglobulins compared to smaller molecules such as albumin, or smaller molecules, such as metabolites. The nature of the analytes may be considered, such as lipids and fatty acids. The movement of fluids and solute in and out of compartments will, in some embodiments, be further estimated based on intravascular pressure in various vascular beds such as arterial versus venous, tissue pressure, hydrostatic pressure, osmotic pressure, oncotic pressure, and transcompartment electrical potential. A person of ordinary skill in the art will understand that the principle applies with respect to various compartments and types of cells: to both endothelial cell lined compartments, epithelial cell lined compartments such as the pancreas, gastrointestinal tract, pulmonary compartments, renal and urological compartments and other barriers. In another embodiment, the estimated state of the patient and the patient trajectory calculator can be used to predict the incremental changes in the compartments over time and the effects of different types of interventions to be reported outside the system to an expert, such as a physician, to make therapeutic decisions. In an embodiment, these calculations may be used to optimize fluid resuscitation based on fluid deficits in the vascular or other compartments to prevent under- or over-resuscitation, and to select the preferred replacement fluid such as a balanced electrolyte solution, with or without albumin, plasma, blood or other therapies.

In another embodiment, the severity calculator uses the patient avatar to detect hypertriglyceridemia and to calculate the predicted effects of elevated triglyceride levels based on the state of the patient to determine treatment regimen. Information including, but not limited to obesity status, diabetes mellitus status, excess alcohol consumption, carbohydrate, fatty acid, lipase, and albumin concentrations may be used to optimize treatments such as insulin infusions to lower triglyceride levels, adding albumin to absorb fatty acids, plasma exchange or related technology, fibrate or statin medications, and monitoring of acidosis. In one embodiment, the calculator can estimate whether the fatty acids likely to be released are more or less toxic than a reference case, based on patient diet and the likely presence of enzymes that affect fatty acid saturation. In an embodiment, risk factors for hypertriglyceridemia are computed as part of a patient's disposition toward recurrent acute pancreatitis, as a likely etiologic factor.

A further embodiment of the severity calculator may monitor patient electrolytes to analyze the patient for acid-based disorders. For example, this could include the physiochemical causes of acidosis, mitochondrial damage, renal failure, respiratory failure, and the like.

In another embodiment, the severity calculator performs a retrospective or prospective analysis to determine patient eligibility in clinical trials. Enrollment in clinical trials is based on guidelines called inclusion criteria and exclusion criteria. The inclusion criteria and exclusion criteria are designed to ensure safety for patients. In some embodiments, the inclusion criteria are designed to identify and thereby enroll healthy patients. In other embodiments, the inclusion criteria are designed to identify and thereby enroll patients having specific diseases or disease states.

One embodiment of the patient severity calculator is associated with a clinical trial for pancreatitis therapeutics. In such an embodiment, a clinical trial may base inclusion criteria from symptoms of one or more of acute pancreatitis, chronic pancreatitis, and necrotizing pancreatitis. When the inclusion criteria are based on symptoms of acute pancreatitis, the symptoms of acute pancreatitis include one or more of abdominal pain, elevated serum amylase levels, elevated serum lipase levels, or imaging findings that display bodily structures associated with pancreatitis. In some embodiments, the severity calculator that is applied to a clinical trial for pancreatitis therapeutics includes criteria that exclude patients based on one or more of extended presence of pain, cancer diagnosis, chronic disease diagnosis, substance abuse, child bearing potential, systemic inflammatory response syndrome (SIRS) diagnosis, mortality risk metrics, age, gender, ancestry, or medical treatment history.

The severity calculator is configured to determine patient eligibility in clinical trials by applying the patient model. The patient model includes static and dynamic information to thereby form a complete description of the status of the patient. The status of the patient is continually updated in the patient state machine, and enrollment eligibility can be generalized as the particular patient state. In one embodiment, a patient trajectory predictor can compute at least one clinical score. The value of the clinical score depends on the patient model, and examples of patient models include SIRS, Bedside Index for Severity in Acute Pancreatitis (BISAP), APACHE II (Acute Physiology, Age, Chronic Health Evaluation II), and combinations of the above. The value of the clinical score that is dependent on the above patient models can, in some embodiments, determine whether a patient should be included or excluded from a clinical trial. In some embodiments, the value of the clinical score determines patient archetypes. The patient archetypes are not limited and include patients that are men, patients that are women, patients over 60 years of age, patients having a body mass index (BMI) of at least about 30 kg/m$^2$, and combinations of one or more of the above. The patient archetypes can be used to determine which patients experience the greatest drug efficacy at a selected therapeutic dose, or which patient archetypes possess the greatest risk of side effects. In some embodiments, different dose ranges correspond to different patient archetypes.

In an embodiment where the severity calculator is linked to electronic medical records, a patient can be determined to be eligible for a clinical trial immediately, as they are admitted to the hospital and their vital signs, laboratory measures, and basic information are acquired. The patient can then provide their informed consent to participate in the clinical trial, and the clinician can forward their information to the study coordinator. In an embodiment where the study coordinator has a large patient pool that has not previously been evaluated, the severity calculator can swiftly identify the eligible subset of the patient pool, minimizing the need for manual ascertainment. In an embodiment, the severity calculator maintains patient confidentiality as patients are enrolled in to trials by masking identifying information and generating unique numerical identifiers.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

The invention claimed is:

1. A severity calculator system for performing at least one patient intervention for acute pancreatitis, comprising:
a device;
a processor; and
a non-transitory processor readable storage medium containing instructions executable by the processor to:
determine a patient state machine by collecting and transforming one or more of patient static measurements and patient dynamic measurements,
determine a patient avatar, the patient avatar being substantially derived from at least one of a patient archetype model and a patient model, wherein the patient avatar is a continuously improving model,
instruct the device to perform at least one test associated with acute pancreatitis including a measurement of blood pressure, respiratory rate, heart rate, serum electrolyte levels, blood urea nitrogen levels, blood creatinine levels, arterial blood gas levels, pH, pulse oximetry, imaging, blood cell count, urine output, fecal output, body temperature, blood sugar measurements, liver injury test, lipid profiles, serum protein levels, albumin levels, hormone levels, metabolome levels, and secretion levels,
determine the trajectory of a patient, wherein:
the trajectory of the patient is one or more of towards a healthy state, towards organ failure, and towards the acute pancreatitis, and
the trajectory of the patient is computed by a patient trajectory predictor,
determine the predicted etiology of the acute pancreatitis, and
determine and output the at least one patient intervention that, when the patient intervention is performed, leads to homeostasis of a patient, wherein the at least one patient intervention is one or more of administering normal saline solution, administering dextrose solution, administering Ringer's lactate solution, administering albumin, administering plasma, or administering a solution of electrolytes,
wherein administering Ringer's lactate solution is disqualified as the at least one patient intervention if the predicted etiology of the acute pancreatitis is hypercalcemia.

2. The severity calculator system of claim 1, wherein the instructions further cause the processor to choose an intervention and communicate with an infusion device.

3. The severity calculator system of claim 1, wherein the instructions further cause the processor to compute a prediction error.

4. The severity calculator system of claim 3, wherein the prediction error includes one or more of a mean square error, a sum of squared errors, a t-statistic, or a rule-based output.

5. The severity calculator system of claim 3, wherein the prediction error is only based on a most recently predicted time point.

6. The severity calculator system of claim 3, wherein the instructions further cause the processor to change the patient avatar based on the computed prediction error.

7. The severity calculator system of claim 1, wherein the patient model comprises at least one submodel selected from a renal model, a liver model, a cardiovascular model, a gastrointestinal model, a nervous system model, an endocrine model, an immune model, a complement model, a kinin model, a fibrinolysis model, a feeding model, and a fluid compartment model.

8. A severity calculator computer program product for determining and instructing at least one patient intervention for acute pancreatitis, comprising:
a storage device having code stored therein, the code being executable by a processor and comprising:

code that determines a patient state machine by collecting and transforming one or more of patient static measurements and patient dynamic measurements, code that determines a patient avatar, the patient avatar being substantially derived from at least one of a patient archetype model and a patient model, wherein the patient avatar is a continuously improving model, code that instructs a device to perform at least one test associated with acute pancreatitis including a measurement of blood pressure, respiratory rate, heart rate, serum electrolyte levels, blood urea nitrogen levels, blood creatinine levels, arterial blood gas levels, pH, pulse oximetry, imaging, blood cell count, urine output, fecal output, body temperature, blood sugar measurements, liver injury test, lipid profiles, serum protein levels, albumin levels, hormone levels, metabolome levels, and secretion levels, code that determines the trajectory of a patient, wherein:

the trajectory of the patient is one or more of towards a healthy state, towards organ failure, towards the disease state, and the trajectory of the patient is computed by a patient trajectory predictor, code that determines the predicted etiology of the acute pancreatitis, and code that determines and outputs the at least one patient intervention that, when the patient intervention is performed, leads to homeostasis of a patient, wherein the at least one patient intervention is one or more of administering normal saline solution, administering dextrose solution, administering Ringer's lactate solution, administering albumin, administering plasma, or administering a solution of electrolytes, wherein administering Ringer's lactate solution is disqualified as the at least one patient intervention if the predicted etiology of the acute pancreatitis is hypercalcemia.

9. The severity calculator computer program product of claim 8, further comprising code that chooses an intervention and code that communicates with an infusion device.

10. The severity calculator computer program product of claim 8, further comprising code that computes prediction error.

11. The severity calculator computer program product of claim 10, wherein the prediction error includes one or more of a mean square error, a sum of squared errors, a t-statistic, or a rule-based output.

12. The severity calculator computer program product of claim 10, wherein the prediction error is only based on a most recently predicted time point.

13. The severity calculator computer program product claim 10, wherein the instructions further cause the processor to change the patient avatar based on the computed prediction error.

14. The severity calculator computer program product of claim 8, wherein the patient model comprises at least one submodel selected from a renal model, a liver model, a cardiovascular model, a gastrointestinal model, a nervous system model, an endocrine model, an immune model, a complement model, a kinin model, a fibrinolysis model, a feeding model, and a fluid compartment model.

15. A method of calculating severity of acute pancreatitis, the method comprising:

determining a patient state machine by collecting and transforming one or more of patient static measurements and patient dynamic measurements, determining a patient avatar, the patient avatar being substantially derived from at least one of a patient archetype model and a patient model, wherein the patient avatar is a continuously improving model, performing at least one test associated with acute pancreatitis including acute pancreatitis including a measurement of blood pressure, respiratory rate, heart rate, serum electrolyte levels, blood urea nitrogen levels, blood creatinine levels, arterial blood gas levels, pH, pulse oximetry, imaging, blood cell count, urine output, fecal output, body temperature, blood sugar measurements, liver injury test, lipid profiles, serum protein levels, albumin levels, hormone levels, metabolome levels, and secretion levels, determining the trajectory of a patient, wherein:

the trajectory of the patient is one or more of towards a healthy state, towards organ failure, towards acute pancreatitis, and the trajectory of the patient is computed by a patient trajectory predictor, determine the predicted etiology of the acute pancreatitis, and performing at least one patient intervention that leads to homeostasis of a patient, the patient intervention comprising one or more of administering normal saline solution, administering dextrose solution, administering Ringer's lactate solution, administering albumin, administering plasma, or administering a solution of electrolytes, wherein administering Ringer's lactate solution is disqualified as the at least one patient intervention if the predicted etiology of the acute pancreatitis is hypercalcemia.

16. The method of claim 15, wherein the patient model comprises at least one submodel selected from a renal model, a liver model, a cardiovascular model, a gastrointestinal model, a nervous system model, an endocrine model, an immune model, a complement model, a kinin model, a fibrinolysis model, a feeding model, and a fluid compartment model.

* * * * *